(12) United States Patent
Xia

(10) Patent No.: US 7,381,762 B2
(45) Date of Patent: Jun. 3, 2008

(54) ULTRAVIOLET LIGHT (UV) ABSORBING COMPOUNDS AND COMPOSITIONS CONTAINING UV ABSORBING COMPOUNDS

(75) Inventor: Jusong Xia, Moore, SC (US)

(73) Assignee: Milliken & Company, Spartanburg, SC (US)

( * ) Notice: Subject to any disclaimer, the term of this patent is extended or adjusted under 35 U.S.C. 154(b) by 208 days.

(21) Appl. No.: 10/922,734

(22) Filed: Aug. 20, 2004

(65) Prior Publication Data

US 2006/0041038 A1 Feb. 23, 2006

(51) Int. Cl.
*C08K 5/3475* (2006.01)
*C07D 249/20* (2006.01)

(52) U.S. Cl. .................. 524/91; 548/257; 548/259; 548/260

(58) Field of Classification Search ................ 524/104, 524/91; 548/257, 259, 260
See application file for complete search history.

(56) References Cited

U.S. PATENT DOCUMENTS

| | | | |
|---|---|---|---|
| 4,853,471 A | 8/1989 | Rody et al. ............. 548/261 |
| 4,973,702 A | 11/1990 | Rody et al. ............. 548/261 |
| 4,973,703 A | 11/1990 | Imuta et al. ............. 548/342 |
| 5,032,498 A | 7/1991 | Rody et al. ............. 430/512 |
| 5,459,222 A | 10/1995 | Rodgers et al. ............ 528/73 |
| 5,585,228 A | 12/1996 | Vishwakarma et al. ..... 430/512 |
| 5,994,431 A | 11/1999 | Olson et al. ............. 524/91 |
| 6,037,393 A | 3/2000 | Okumura et al. ............. 524/91 |
| 6,150,440 A | 11/2000 | Olson et al. ............. 524/91 |
| 6,268,415 B1 * | 7/2001 | Renz et al. ............. 524/91 |
| 6,291,586 B2 | 9/2001 | Lasch et al. ............. 525/123 |
| 6,307,055 B1 | 10/2001 | Thanki et al. ............. 548/259 |
| 6,653,484 B2 | 11/2003 | Toan et al. ............. 548/259 |

FOREIGN PATENT DOCUMENTS

| | | | |
|---|---|---|---|
| EP | 0 627 452 | 12/1998 | ............. 18/38 |
| JP | 2001-287439 | 10/2001 | |

\* cited by examiner

*Primary Examiner*—Kriellion A Sanders
(74) *Attorney, Agent, or Firm*—Terry T. Moyer; Robert M. Lanning

(57) ABSTRACT

Hydroxybenzotriazole-based compounds are useful for ultraviolet light absorbing additives for a variety of applications. Such compounds have particular usefulness in various applications, including plastics, automotive, coatings, and food packaging applications. Such inventive compound exhibit excellent UV radiation absorbing activity, high thermal stability, excellent low fogging, low extraction/low migration rates, and high lightfastness levels, particularly when incorporated within certain media and/or on the surface of certain substrates, particularly polyesters, polyolefins, and polyurethanes. Block copolymer chain or chains consisting of poly(oxyalkylene) and/or aliphatic polyester segments can be conveniently tailored to increase the solubility or compatibility in different solvents or resins thereby permitting the introduction of such excellent UV absorbing chromophores within diverse media and/or or diverse substrates. Compositions and articles comprising such compounds are provided as well as methods for producing such inventive compounds.

32 Claims, No Drawings

ULTRAVIOLET LIGHT (UV) ABSORBING COMPOUNDS AND COMPOSITIONS CONTAINING UV ABSORBING COMPOUNDS

BACKGROUND OF THE INVENTION

Ultraviolet absorbing compounds have many uses and industrial applications. Such compounds are useful in combination with various polymers, including for example polyurethanes, polyolefins, PET, and the like for protecting the polymers or products made with the polymers against degradation by exposure to ultraviolet light.

U.S. Pat. Nos. 5,994,431; 6,150,440 and 6,291,586 are directed to amide functional benzotriazole UV absorbers and their application in polyolefin, polyurethane and other films. U.S. Pat. No. 5,459,222 to Rodgers reports UV absorbing polyurethanes and polyesters obtained by reacting difunctional (i.e. two —OH groups) benzotriazole UV absorbers with polyurethane or polyester monomers.

U.S. Pat. No. 6,307,055 to Thanki et al discloses a diol-functionalized benzotriazole UV absorbers prepared from bromobenzotriazole precursor and di(hydroxyalkyl) amine.

U.S. Pat. Nos. 4,857,471; 4,973,702 and 5,032,498 disclose amide functional benzotriazole UV absorbers. U.S. Pat. No. 5,585,228 discloses a specific benzotriazole derivative as photographic element. This specific UV absorbers are obtained from the reaction of the 4-OH group on 2H-(2,4-dihydroxyphenyl)benzotriazole with glycidyl ethers.

U.S. Pat. No. 6,037,393 to Okumura reports novel polyester compounds having benzotriazole group(s) obtained by ring-opening polymerization of lactones with hydroxyalkylphenyl benzotriazoles.

U.S. Pat. Nos. 6,653,484 and 6,369,267 to Toan et al. disclose benzotriazole derivatives which are substituted or bridged with polyoxyalkylene groups obtained from the reaction of benzotriazole precursors with alkyl caped polyethylene glycol glycidyl ether.

DETAILED DESCRIPTION OF THE INVENTION

Reference now will be made to the embodiments of the invention, one or more examples of which are set forth below. Each example is provided by way of explanation of the invention, not as a limitation of the invention. In fact, it will be apparent to those skilled in the art that various modifications and variations can be made in this invention without departing from the scope or spirit of the invention.

The invention is directed to UV absorbing compounds that can be used in a wide variety of compositions or end products to provide to a coating, substrate, or resin a UV resistant property. Ultraviolet light degrades many substances, and thus a composition that can be used to avoid such undesirable degradation is highly desirable.

Benzotriazole derivatives set forth herein are in general reactive, liquid, and are polymeric-bearing amide functioning oxyalkylene and aliphatic ester block copolymer/oligomer chain(s). The inventive UV absorbers set forth herein typically are liquid and polymeric, but it is not required that they be liquid, or polymeric.

The inventive UV absorbers, in one particular embodiment, bear primary OH group(s) at the end of the respective polymer chain(s). They may be completely reactive in polyurethane, PET and polycarbonate (PC) applications, for example. One advantage of the invention is that the inventive UV absorbers tend to resist extraction, migration, fogging, and leaching. Furthermore, they may provide longer performance lifetimes than conventional UV absorbers in many applications.

The inventive UV absorbers may bear oxyalkylene (hydrophilic) and aliphatic ester (hydrophobic) functions, thus usually these compositions are adjustable within the combination to provide compatibility for various media. The inventive UV absorbers (when used in combination with other additives) may offer a very good solution to stabilize polyurethane from $NO_x$ gas fading, which is highly desirable.

The invention, in one embodiment, may comprise ultraviolet light absorbing compound having the structure represented by

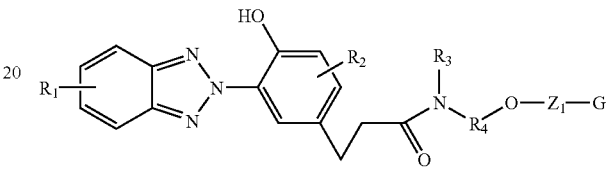

wherein:

$R_1$ is selected from the group of: H, F, Cl, Br, I, alkyls, alkoxy, C=O containing radicals represented as —C(O)-A, and $SO_2$-containing radicals represented as $SO_2$-A, wherein A is OH, alkyl, alkoxy, or an organic amine group;

$R_2$ is selected from the group of: H, $C_1$-$C_{10}$ alkyls, or $C_7$-$C_{20}$ phenylalkyls;

$R_3$ is selected from the group of: H, carbon and/or oxygen and/or nitrogen containing chain radicals; and $R_4$ is selected from the group of: divalent $C_2$-$C_{20}$ alkyl radicals, divalent $C_4$-$C_{20}$ alky radicals which are interrupted by oxygen, sulfur or nitrogen, and divalent oligomeric radicals; and G is selected from one of the following: H, $C_1$-$C_{10}$ alkyls, alkyl carbonyls, and aryl carbonyl groups; and $Z_1$ is selected from (a) or (b) below:

(a) $C_2$-$C_{10}$ alkyls;

(b) divalent radicals represented by:

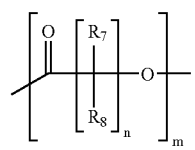

wherein:

$R_7$ and $R_8$ each are independently selected from H or $C_1$-$C_{10}$ alkyl groups;

n comprises an integer between 1 and 10;

m comprises any positive integer or fraction between 1 and 20.

Furthermore, a compound is provided in one aspect of the invention wherein $R_3$ comprises a carbon and/or oxygen and/or nitrogen-containing chain radical represented by:

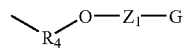

wherein:

$R_4$, $Z_1$, and G are as defined above.

In some applications of the invention, a compound is provided in which $R_4$ is a divalent oligomeric radical represented by:

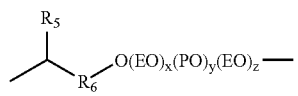

wherein

EO comprises ethylene oxide or a derivative thereof;
PO comprises propylene oxide or a derivative thereof; and
$R_5$ comprises H or $C_1$-$C_{10}$ alkyl groups;
$R_6$ comprises a divalent $C_1$-$C_{10}$ alkyl radical;
wherein x, y, and z comprise positive integers or fractional numbers between 0 and 20, and further
wherein x+y+z is equal to or greater than 1.

$R_1$ and $R_2$, in some embodiments, may be bonded to specific respective carbons, as shown below:

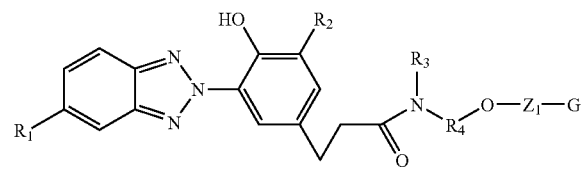

wherein $R_1$, $R_2$, $R_3$, $R_4$, $Z_1$ and G are as previously described.

A compound of the invention may also be represented by the formula:

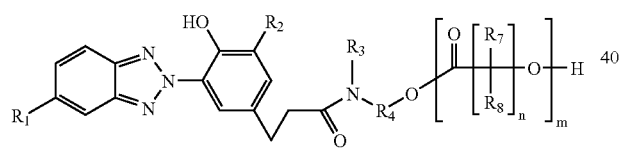

wherein:

$R_1$ is selected from the group of: H, F, Cl, Br, I, alkyls, alkoxy, —C(O)-A and —SO$_2$-A wherein A is OH, alkyl, alkoxy, or an organic amine group;

$R_2$ is selected from the group of: H, $C_1$-$C_{10}$ alkyls, and $C_7$-$C_{20}$ phenylalkyls;

$R_3$ is selected from the group of: H, carbon and/or oxygen and/or nitrogen-containing chain radicals; and $R_4$ is selected from the group of: divalent $C_2$-$C_{20}$ alkyl radicals, divalent $C_4$-$C_{20}$ alky radicals which are interrupted by oxygen, sulfur or nitrogen, and divalent oligomeric radicals; and $R_7$ and $R_8$ each are independently selected from the group of: H and $C_1$-$C_{10}$ alkyl groups;

n comprises an integer between 1 and 10; and m comprises a positive integer or fraction between 1 and 20.

The invention, in one aspect, may provide an ultraviolet light absorbing compound adapted for incorporation into polymers, said compound being comprised of a benzotriazole moiety and at least one reactive moiety bonded to said benzotriazole moiety, said reactive moiety being capable of reacting with said polymer under conditions to facilitate substantial non-migration of said compound within polymer, said reactive moiety having at least one reactive —OH group, further wherein said compound comprises a liquid or a paste at a temperature of up to about 45 degrees C. The reactive moiety may comprise: (a) a proximal portion adjacent to and bonded to said benzotriazole moiety, and (b) a distal portion positioned apart from said benzotriazole moiety, wherein said —OH group is positioned upon said distal portion. The reactive moiety may comprise an amine or an amide. The amine may comprise a tertiary amine. The reactive moiety further may comprise an oxyalkylene or a derivative thereof. The reactive moiety comprises at least one aliphatic portion. The aliphatic portion further may comprise a copolymeric chain. The aliphatic portion may comprise a block copolymer.

In one aspect of the invention, an ultraviolet light absorbing compound may be adapted for incorporation into polymers. The compound may be comprised of a benzotriazole moiety and at least one reactive moiety bonded to the benzotriazole moiety. The reactive moiety may be capable of reacting with the polymer under conditions to facilitate substantial non-migration of the compound within polymer. The reactive moiety has at least one reactive —OH group, further wherein said compound is a liquid or a paste at a temperature of up to about 45 degrees C. The reactive moiety may (in some applications) comprise (a) a proximal portion adjacent to and bonded to said benzotriazole moiety, and (b) a distal portion positioned apart from said benzotriazole moiety. An —OH group may be positioned upon the distal portion, as defined.

The compound(s) of the invention may be made in part by the process of reacting (a) and (b), as further set forth below:

(a) the compound having the structure represented as the following

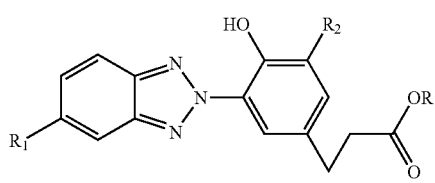

wherein:

$R_1$ and $R_2$ are independent and are defined as above;

R is a group selected from hydrogen, alkyl and aryl; and (b) an organic amine as represented as

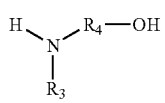

In one embodiment of the invention, the compound may be made by reacting the compound set forth in (a) with said amine in (b) to make an intermediate or a product, said intermediate or product being illustrated as the following

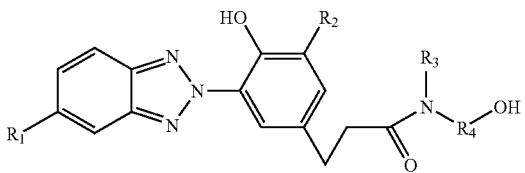

wherein:

$R_1$, $R_2$, $R_3$, and $R_4$ are defined as above.

In yet another embodiment of the invention, the compound(s) may be formed in part by making said intermediate, further wherein said intermediate of said process is further reacted with m equivalents of cyclic lactones/esters represented as the following structure

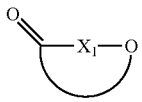

wherein $X_1$ is a divalent radical selected from the group of: $C_2$-$C_{20}$ aryls, and alkyls as represented by the following

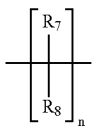

wherein: n, m, $R_7$ and $R_8$ are defined as above.

Thus, those reactions result in the ultraviolet light absorbing compound of the invention, in some embodiments.

An article may be provided in the invention which includes:

(a) at least one polymeric formulation having a thermoplastic or thermoset component, or mixtures thereof; (b) at least one UV absorber compound, either i) present within said polymeric formulation or ii) adhered to the surface of said polymeric formulation. In one aspect of the invention, the UV absorber compound may comprise a benzotriazole derivative, further wherein at least one alkyl chain which is interrupted by oxygen, sulfur or nitrogen; and a poly(oxyalkylene) chain, aliphatic polyester chain, or block copolymeric chain, consisting of poly(oxyalkylene) and aliphatic polyester segments. The segments being attached to said UV absorber compound by way of an amide functional group.

The compounds according to the invention may be effective light stabilizers for organic materials, for example for coatings and a large number of polymers. For all applications in which a liquid, oligomeric and non-migration properties are highly desirable, the inventive compounds afford advantages over conventional UV absorbers. These polymers may be polyurethane, polyolefin, PET and other polyester, polycarbonate, polyamide, and the like. Some representative polymers are provided as such: polymers of monoolefines and diolefines, for example polyethylene (which can, if desired, be crosslinked), polypropylene, polyisobutylene, polybut-1-ene, polymethylpent-1-ene, polyisoprene or polybutadiene, and also polymers of cycloolefines, for example polymers of cyclopentene or norbornene; mixtures of such polymers, for example, mixtures of polypropylene with polyethylene or polyisobutylene.

Copolymers of monoolefines or diolefines with one another or with other vinyl monomers, for example ethylene/propylene copolymers, propylene/but-1-ene copolymers, propylene/isobutylene copolymers, ethylene/but-1-ene copolymers, propylene/butadiene copolymers, isobutylene/isoprene copolymers, ethylene/ethyl acrylate copolymers, ethylene/alkyl methacrylate copolymers, ethylene/vinyl acetate copolymers or ethylene/acrylic acid copolymers and salts thereof (ionomers), and also terpolymers of ethylene with propylene and a diene, such as hexadiene, dicyclopentadiene or ethylidenenorbornene, random copolymers of styrene or alpha.-methylstyrene with dienes or acrylic derivatives, for example styrene/butadiene, styrene/acrylonitrile, styrene/ethyl methacrylate or styrene/acrylonitrile/methacrylate; mixtures of high impact strength obtained from styrene copolymers and another polymer, for example a polyacrylate, a diene polymer or an ethylene/propylene/diene terpolymer; and also block copolymers of styrene, for example styrene/butadiene/styrene, styrene/isoprene/styrene, styrene/ethylene-butylene/styrene or styrene/ethylene-propylene/styrene; graft copolymers of styrene, for example styrene on polybutadiene, styrene and acrylonitrile on polybutadiene, styrene and alkyl acrylates or alkyl methacrylates on polybutadiene, styrene and acrylonitrile on ethylene/propylene/diene terpolymers, styrene and acrylonitrile on polyalkyl acrylates or polyalkyl methacrylates, styrene and acrylonitrile on acrylate/butadiene copolymers and mixtures thereof with the copolymers mentioned under 5), such as are known as so-called ABS, MBS, ASA or AES polymers; halogen-containing polymers, for example polychloroprene, chlorinated rubber, chlorinated or chlorosulfonated polyethylene and especially polymers formed from halogen-containing vinyl compounds, for example polyvinyl chloride, polyvinylidene chloride, polyvinyl fluoride and polyvinylidene fluoride and also copolymers thereof, such as vinyl chloride/vinylidene chloride, vinyl chloride/vinyl acetate or vinylidene chloride/vinyl acetate; polymers derived from .alpha.,.beta.-unsaturated acids and derivatives thereof, such as polyacrylates and polymethacrylates, polyacrylamides and polyacrylonitriles; including also copolymers of the monomers above, with one another or with other unsaturated monomers, for example acrylonitrile/butadiene copolymers, acrylonitrile/alkyl acrylate copolymers, acrylonitrile/vinyl chloride copolymers or acrylonitrile/alkyl methacrylate/butadiene terpolymers; polymers derived from unsaturated alcohols and amines or acyl derivatives or acetals thereof, such as polyvinyl alcohol, polyvinyl acetate, polyvinyl stearate, polyvinyl benzoate, polyvinyl maleate, polyvinyl butyral, polyallyl phthalate or polyallylmelamine; homopolymers and copolymers of cyclic ethers, such as polyalkylene glycols, polyethylene oxide or polypropylene oxide or copolymers thereof with bisglycidyl ethers; polyacetals, such as polyoxymethylene and also polyoxymethylenes containing comonomers such as ethylene oxide; polyphenylene oxides and sulfides and also mixtures of polyphenylene oxides and polystyrene; polyurethanes derived, on the one hand, from polyethers, polyesters and polybutadienes having terminal hydroxyl groups and, on the other hand, from aliphatic or aromatic polyisocyanates, and also precursors thereof; polyamides and copolyamides derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethylene terephthalamide and polym-phenylene isophthalamide, and copolymers thereof with polyethers, for example copolymers with polyethylene glycol, polypropylene glycol or polytetramethylene glycol.

Product and End Use Applications

Appropriately stabilized compositions are thus a preferred form of the compositions mentioned above. It is preferable to stabilize polyurethane and coatings formed from polymers of any appropriate types in any suitable applications, such as automotive, textile, and exterior and interior of constructions.

The invention may be used when there are risks in being exposed to a light such as sunlight and ultraviolet rays. Specifically, this means that they can be used as glass-substitute products or as glass coating, for houses, equipment, for windows of means of transport, as a coating for lighting glass and for light-sources protecting glass, as an internal or external painting for means of transport, as a material to produce light sources such as florescent lamps or mercury lamps which emit ultraviolet-rays, for producing precise devices, as a material for electrical or electronic devices.

Further, applications include a material containing compositions useful for cutting off electromagnetic waves or the like which are generated by a variety of displays, for food, for chemicals, pharmaceuticals, as a coating or a container of pharmaceuticals. The compositions of the present invention may be used to produce sheets or films that may be used in the agricultural field. The compositions of the present invention may be used for printing materials, such as colorants, in cosmetics for preventing fading, in creams for stopping sunburn, in shampoos or rinses, or other hair care products, in sponge wears, stockings, for making fibers used to manufacture clothes or other articles such as hats or the like, curtains, carpets, for furniture such as wall paper, for plastic lenses, contact lenses, artificial eyes or other medical devices, optical filters, prisms, mirrors, optical articles for photographic material, tapes, ink or other stationery articles, for marker boards, or as a coating for the surface of marking devices.

The stabilizing compounds are incorporated into the organic material by the conventional methods, for example in any desired phase during the manufacture of shaped products. They can, for example, be mixed in the form of a liquid, a paste, a powder with other materials, suspensions or emulsions or solutions into the polymer, which can be in the form of a powder, melt, solution, suspension or emulsion.

Concentrations and Compositions

The stabilizer mixtures of the invention can, if desired, contain 0.1 to 15% by weight, preferably 0.3 to 8% by weight, relative to the polymer, of the customary additives, in particular antioxidants, other UV absorbers such as benzotriazole-, hydroxyl benzophenone- or phenyl triazine-based, other types of light stabilizers or mixtures thereof.

In stabilizing polyurethane foam in particular, the inventive compounds can be used with the following classes of additives:

Class A: Benzotriazoles are (in general) those compounds that conform to the structure represented as the following:

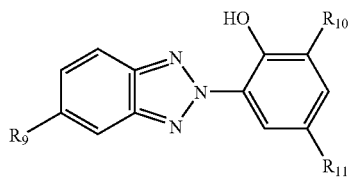

wherein $R_9$, $R_{10}$, and $R_{11}$ are individually selected from hydrogen, a group having a formula $C_aH_bN_cO_dS_e$ wherein a, b, c, d, and e are from 0 to 30, and halogen.

Class B: Hindered phenols or BHT derivatives, and related compounds typically conform to the structure of the following:

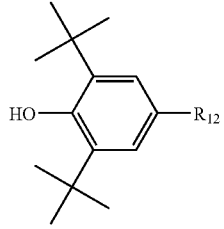

wherein $R_{12}$ is selected from the group consisting of hydrogen, a group having a formula $C_aH_bN_cO_dS_e$ wherein a, b, c, d, and e may be from 0 to 30, and halogen.

Class C: Secondary diphenylamines may conform to the structure of the following

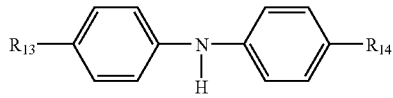

wherein $R_{13}$ and $R_{14}$ are individually selected from the group consisting of hydrogen, a group having a formula $C_aH_bN_cO_dS_e$ wherein a, b, c, d, and e are from 0 to 30, and halogen.

Class D: Lactone-based antioxidants may include those compounds that conform to the structure of the following:

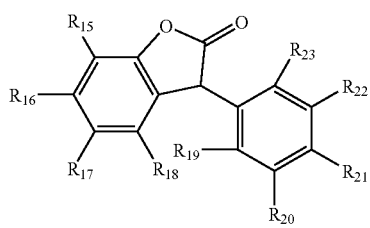

wherein $R_{15}$ to $R_{23}$ are individually selected from the group consisting of hydrogen, a group having a formula $C_aH_bN_cO_dS_e$ wherein a, b, c, d, and e are from 0 to 30, and halogen.

The following examples are illustrative of the invention, but do not in limit the scope of the invention. Species provided below may enable a person of skill in the art to practice the entire chemical genus represented by the specific species presented below.

SYNTHETIC EXAMPLES OF THE INVENTION

Example 1

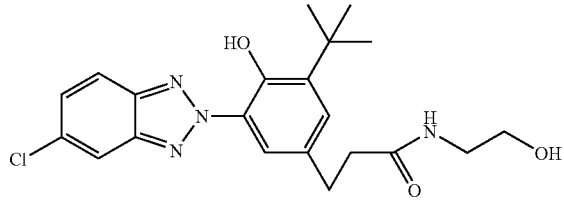

A 100 mL 3-neck round-bottom flask equipped with a mechanical stirrer, a thermal controller and a reflux condenser was charged with about 20 g (51 mmol) of 3-(5-chloro-2H-benzotriazol-2-yl)-5-(1,1-dimethylethyl)-4-hydroxy-benzenepropanoic acid methyl ester, 4.4 g (1.4 eq) of ethanolamine and 100 ml of xylene. The reaction was heated to 130 C under N2 blank and monitored. After about eight (8) hours, the reaction was completed. Upon cool down to 5-10° C., the solid precipitate was collected by filtration, and washed with cold methylene chloride and dried overnight. 20.5 g of analytical pure product was obtained with a melting point (mp) of about 132-135 C, and an NMR (CDCl3): 11.51 (broad,1H), 8.06 (s,1H), 7.89 (s, 1H), 7.85 (d, 1H), 7.41 (d, 1H), 7.21 (s, 1H), 6.06 (m, 1H), 3.70 (t, 2H), 3.41 (m, 2H), 3.01 (t, 2H), 2.56 (t, 2H), 1.48 (s, 9H).

Example 2

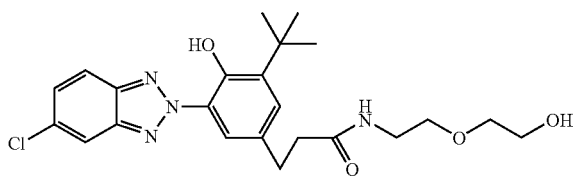

To a 250 mL 3-neck round-bottom flask equipped with a mechanical stirrer, a thermal controller and a reflux condenser, were charged 54.5 g (141 mmol) of 3-(5-chloro-2H-benzotriazol-2-yl)-5-(1,1-dimethylethyl)-4-hydroxy-benzenepropanoic acid methyl ester and 21.8 g (1.4 eq) of diglycolamine. After 6 hours of heating to 130-135° C. with $N_2$ sweep, TLC suggested there was still trace amount of starting material presence. 2.6 g (0.2 eq) of diglycolamine was added and the heating was continued for 2 more hours. TLC analysis suggested the reaction was completed. Upon cool down to room temperature, 250 ml of methylene chloride was introduced into the reaction mixture, and the solution was washed three times with 3×75 ml of 3% aqueous HCl and then once with 75 ml of water. The organic layer was collected and dried with $MgSO_4$ and the solvent was removed by rotary evaporator. 56 g of analytical pure product was obtained as a pale yellow solid with a mp 84-87° C., and NMR (CDCl$_3$): 11.52 (s, 1H), 8.07 (s, 1H), 7.89 (s, 1 H), 7.85 (d, 1H), 7.40 (d, 1H), 7.21 (s, 1H), 6.16 (m, 1H), 3.69 (t, 2H), 3.55 (m, 6H), 3.00 (t, 2H), 2.55 (t, 2H), 1.48 (s, 9H).

Example 3

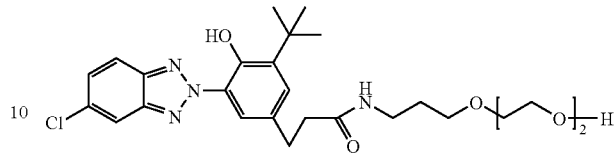

To a 100 mL 3-neck round-bottom flask equipped with a mechanical stirrer, a thermal controller and a reflux condenser, were charged 20 g (51 mmol) of 3-(5-chloro-2H-benzotriazol-2-yl)-5-(1,1-dimethylethyl)-4-hydroxy-benzenepropanoic acid methyl ester and 12 g (1.4 eq) of polyglycolamine H-163 (available from Dixie Chemical). The reaction mixture was heated to 130-135° C. for 6 hours with $N_2$ sweep. TLC analysis suggested the reaction was completed. Upon cool down to room temperature, 120 ml of methylene chloride was introduced into the reaction mixture, and the solution was washed three times with 3×40 ml of 3% aqueous HCl and then once with 40 ml of water. The organic layer was collected and dried with MgSO4 and the solvent was removed by rotary evaporator. 22 g of analytical pure product was obtained as a paste, with proton NMR (CDCl$_3$): 11.51 (s, 1H), 8.08 (s, 1H), 7.90 (s, 1H), 7.85 (d, 1H), 7.41 (d, 1H), 7.22 (s, 1H), 6.28 (m, 1H), 3.71 (t, 2H), 3.57 (m, 4H), 3.49 (m, 4H), 3.00 (t, 2H), 2.52 (t, 2H), 1.48 (s, 9H).

Example 4

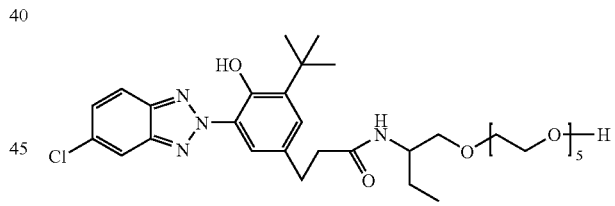

To a 250 mL 3-neck round-bottom flask equipped with a mechanical stirrer, a thermal controller and a reflux condenser, were charged 20 g (51 mmol) of 3-(5-chloro-2H-benzotriazol-2-yl)-5-(1,1-dimethylethyl)-4-hydroxy-benzenepropanoic acid methyl ester and 22 g (1.4 eq) of 2-amino-1-butanol 5EO [1-poly(oxyethylene)oxy-2-aminobutane, Mw 309, prepared in Milliken lab]. The reaction mixture was heated to 130-135° C. for 6 hours with N2 sweep. TLC analysis suggested the reaction was completed. Upon cool down to room temperature, 150 ml of methylene chloride was introduced into the reaction mixture, and the solution was washed three times with 3×40 ml of 3% aqueous HCl and then once with 40 ml of water. The organic layer was collected and dried with $MgSO_4$ and the solvent was removed by rotary evaporator. 30 g of product was obtained as a pale yellow liquid which was confirmed by NMR and IR.

Example 5

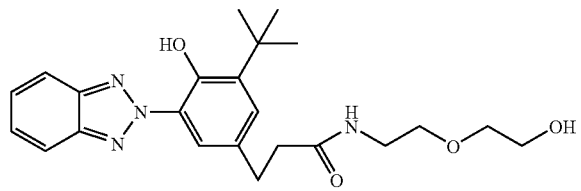

To a 100 mL 3-neck round-bottom flask equipped with a mechanical stirrer, a thermal controller and a reflux condenser, were charged 30 g (85 mmol) of 3-(2H-benzotriazol-2-yl)-5-(1,1-dimethylethyl)-4-hydroxy-benzenepropanoic acid methyl ester and 14.2 g (1.6 eq) of diglycolamine. After 9 hours of heating to 130-135 C with $N_2$ sweep, TLC analysis suggested the reaction was completed. Upon cool down to room temperature, 200 ml of methylene chloride was introduced into the reaction mixture, and the solution was washed three times with 3×50 ml of 3% aqueous HCl and then once with 50 ml of water. The organic layer was collected and dried with $MgSO_4$ and the solvent was removed by rotary evaporator. 32 g of product was obtained as a viscous liquid, which upon standing in −5° C. overnight become a pale solid with the mp of 106-109° C. Product purity was confirmed by NMR.

Example 6

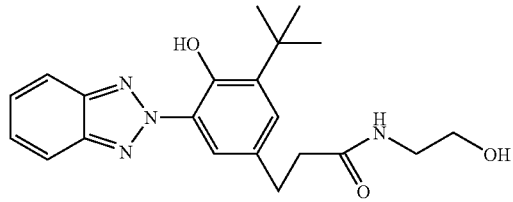

Accordingly, the title product was prepared from the reaction of 30 g (85 mol) of 3-(2H-benzotriazol-2-yl)-5-(1,1-dimethylethyl)-4-hydroxy-benzenepropanoic acid methyl ester with 8.3 g (1.6 eq) of ethanolamine, using the similar procedure as described in Example 5. Product purity was confirmed by NMR and directly used as intermediate for further reaction with purification.

Example 7

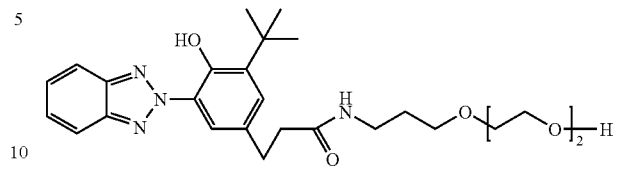

Accordingly, the title product was prepared from the reaction of 30 g (85 mol) of 3-(2H-benzotriazol-2-yl)-5-(1,1-dimethylethyl)-4-hydroxy-benzenepropanoic acid methyl ester with 19.4 g (1.4 eq) of polyglycolamine H-163, using similar procedure as described in Example 3. Product purity was confirmed by NMR and directly used as intermediate for further reaction with purification.

Example 8

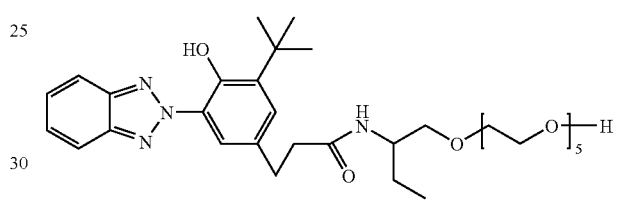

Accordingly, the title product was prepared as a viscous liquid from the reaction of 30 g (85 mol) of 3-(2H-benzotriazol-2-yl)-5-(1,1-dimethylethyl)-4-hydroxy-benzenepropanoic acid methyl ester with 36.8 g (1.4 eq) of 2-amino-1-butanol 5EO [1-poly(oxyethylene)oxy-2-amino-butane, Mw 309, prepared in Milliken lab], using similar procedure as described in Example 4. Product purity was confirmed by NMR and IR.

Example 9

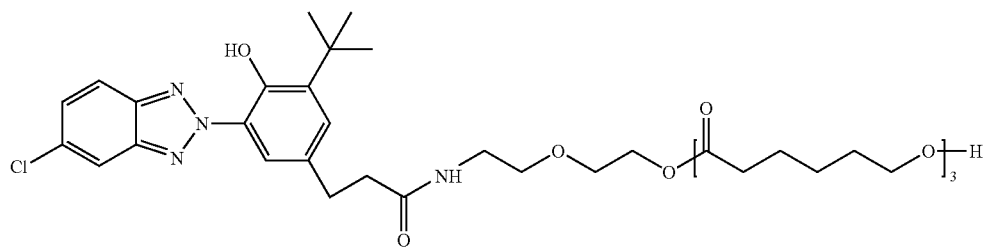

To a 500 mL 3-neck round-bottom flask equipped with a mechanical stirrer, a thermal controller and a reflux condenser, were charged 100 g (217 mmol) of benzotriazole intermediate prepared in Example 2, 74 g (3 eq) of caprolactone, and 1 g of 50% hypophosphorous acid. The reaction mixture was heated to 100° C. under $N_2$ for 3 hours. 174 g of product was obtained as pale yellow liquid with a color value/absorbance value of 20.1 abs./g/L (in MeOH) at 347 nm. 71% of transesterificaton rate was obtained based on HPLC analysis. NMR (CDCl$_3$) and IR (on NaCl plate) confirmed the product purity.

Example 10

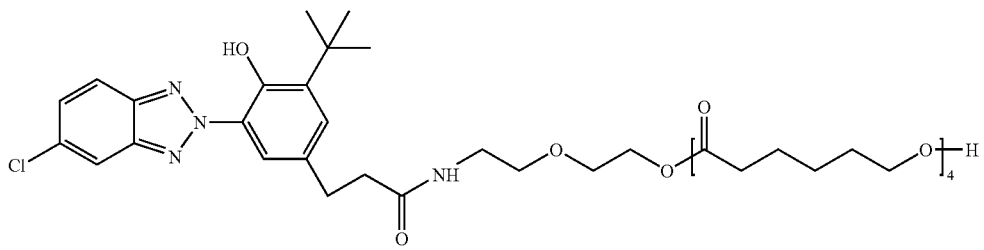

To a 100 mL 3-neck round-bottom flask equipped with a mechanical stirrer, a thermal controller and a reflux condenser, were charged 20 g (43 mmol) of benzotriazole intermediate prepared in Example 2, 19.8 g (4 eq) of caprolactone, and 0.08 g of Fascat® FC9102 (available from Atofina Chemical). The reaction mixture was heated to 140-150° C. under N$_2$ for 1-2 hours. 37 g of product was obtained as pale yellow liquid with a color value/absorbance value of 17.8 abs./g/L (in MeOH) at 347 nm. 78% of transesterificaton rate was obtained based on HPLC analysis.

Example 11

To a 100 mL 3-neck round-bottom flask equipped with a mechanical stirrer, a thermal controller and a reflux condenser, were charged 20 g (47 mmol) of benzotriazole intermediate prepared in Example 5, 16 g (3 eq) of caprolactone, and 0.2 g of 50% hypophosphorous acid. The reaction mixture was heated to 100° C. under N$_2$ for 3 hours. The mixture was cool down to room temperature and dissolved into 150 ml of methylene chloride. The solution was washed twice with 50 ml of water and dried over MgSO$_4$. Upon removing solvent, 33 g of product was obtained as pale liquid with a color value/absorbance value of 17.6 abs./g/L (in MeOH) at 339 nm. 75% of transesterificaton rate was obtained based on HPLC analysis.

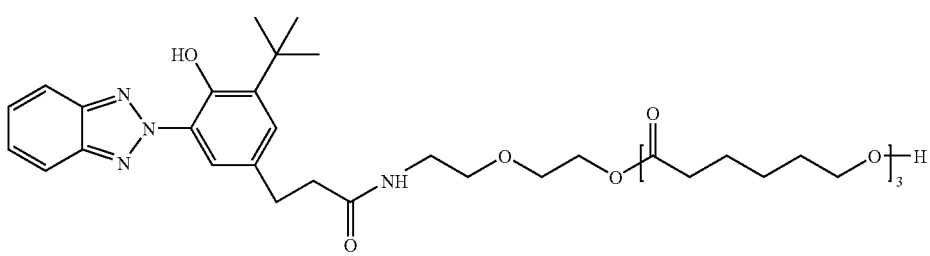

Example 12

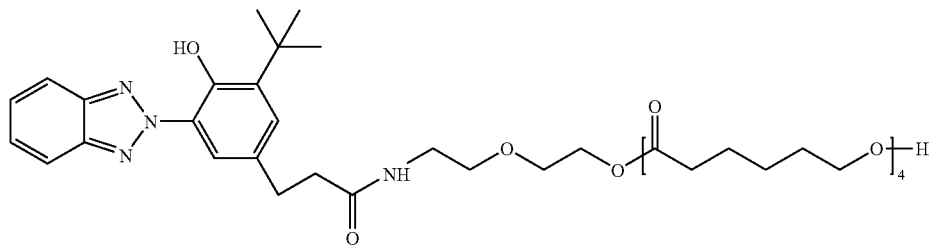

Following the procedure as decribed in Example 11, the title product was prepared from 20 g (47 mmol) of benzotriazole intermediate prepared in Example 5, and 21.4 g (4 eq) of caprolactone, and 0.2 g of 50% hypophosphorous acid. 28 g of product was obtained as pale yellow liquid with a color value/absorbance value of 16.4 abs./g/L (in MeOH) at 339 nm. 72% of transesterificaton rate was obtained based on HPLC analysis.

Article Production and Performance Testing for Various Inventive Liquid Polymeric Benzotriazole UV Absorbers a) Polyether Foam Article Formation The inventive UV absorbers were incorporated with or without other additives to produce (in one particular embodiment of the invention) polyurethane foam in accordance with the following formulation and procedure:

| Component | Amount |
| --- | --- |
| F3022 Polyol (from Arco Chemical) | 100 grams |
| Water | 4.53 ml |
| DABCO 33LV (catalyst, from Air Products) | 0.15 ml |
| DABCO T10 (catalyst) | 0.32 ml |
| L520 Silicone (from Union Carbide) | 1.0 mL |
| 80/20 Toluene diisocyanate (Bayer)(112 index) | 49.0 ml |
| ReacTint ® Blue X3LV | as noted |
| Inventive UV Absorber | as noted |
| Additive from Class A (UV absorbers) | |
| Comparative (Tinuvin ® 326) | as noted |
| Comparative (Tinuvin ® 1130) | as noted |
| Additive from Class B | |
| Irganox ® 1135 | as noted |
| Additive from Class C | |
| Irganox ® 5057 | as noted |
| Additive from Class D | |
| Irganox ® HP 136 | as noted |

Upon mixture within a reaction vessel, the reaction created a "health" bubble (indicating gelation and blowing balance), and the vessel was then exposed to 185° C. (generated within a microwave oven to simulate actual heat history encountered on an industrial production environment) for about 10 min to form a foam bun. The resultant foam buns were then analyzed for performance, as discussed in details below.

b) Performance Characteristics of Polyether Foams Including Inventive UV Absorbers The white foams made in accordance with formulation and process as described in Section a), were all tested for standard foam performance, in terms of rise time, tack time, and bun height, and compared with the control polyether foams either made with existing commercial UV absorbers or made without additive. Measurements within 5% of the control are considered acceptable for the finished foam product. The measurements are summarized in Table 1.

TABLE 1

Foam Performance of Inventive or Comparative UV Absorbers

| Sample Foam # | UV Additive (Mw) | Loading (php) | Rise Time (minutes) | Tack Time (minutes) | Bun Height (mm) |
| --- | --- | --- | --- | --- | --- |
| A1 | N/A | N/A | 1.50 | 3 | 226 |
| A2 | Tinuvin 326 (Mw 316) | 1.5 | 1.55 | 3 | 231 |
| A3 | Tinuvin 1130 (Mw 633) | 1.5 | 1.52 | 3 | 234 |
| A4 | Tinuvin 1130 (Mw 633) | 3.0 | 1.52 | 3 | 235 |
| A5 | Example 9 (Mw 803) | 1.5 | 1.50 | 3 | 232 |
| A6 | Example 9 (Mw 803) | 3.8 | 1.56 | 3 | 233 |
| A7 | Example 11 (Mw 768) | 1.5 | 1.47 | 3 | 231 |
| A8 | Example 11 (Mw 768) | 3.6 | 1.56 | 3 | 235 |

Additionally, the foams produced exhibited good resiliency and densities measured at about 1.5 pounds per cubit foot. Thus, the inventive UV absorbers provide acceptable polyurethane foam articles as compared with control samples.

c) Extraction Measurements From Polyurethane Foams

The polyurethane foams produced in above section b) were analyzed for extraction levels using the following method. The extraction test involved cutting 1 gram of the curred foam from the center of the sample and post-curring the cut foam for another 20 minutes at 160° C. in a glass jar. After cooling to room temperature, 75 grams of methanol were then added to the glass jar that was then capped for 1 hour. The foam was then removed and the extract solution was analyzed under Perkin Elmer Lambda 35 UV-vis spectrophotometer for the maximum absorption. If the solution is too concentrate, dilute it with methanol to 20%, then measure its UV-vis and calculate the absorption value of the original solution. The results are summarized in Table 2.

TABLE 2

Foam Extraction Tests of Inventive or Comparative UV Absorbers

| Sample Foam # | UV Additive (Mw) | Loading (php) | Extraction (Absorbance) | Absorption Max (nm) |
|---|---|---|---|---|
| A1 | N/A | N/A | Not detectable | N/A |
| A2 | Tinuvin 326 (Mw 316) | 1.5 | 4.228 | 348 nm |
| A3 | Tinuvin 1130 (Mw 633) | 1.5 | 1.273 | 340 nm |
| A4 | Tinuvin 1130 (Mw 633) | 3.0 | 2.506 | 340 nm |
| A5 | Example 9 (Mw 803) | 1.5 | 0.273 | 347 nm |
| A6 | Example 9 (Mw 803) | 3.8 | 0.694 | 347 nm |
| A7 | Example 11 (Mw 768) | 1.5 | 0.281 | 340 nm |
| A8 | Example 11 (Mw 768) | 3.6 | 0.652 | 340 nm |

Based on the molecular weight of these additives, 1.5 php of Tinuvin 326 is mole equivalent to 3.0 php of Tinuvin 1130, 3.8 php of inventive Example 9, and 3.6 php of inventive Example 11. As suggested from Table 2, the inventive liquid polymeric UV absorbers provide significant improvement in the foam extraction test, comparing to comparative examples such as commercial products Tinuvin 326 and Tinuvin 1130.

d) Protection of Colorants from UV Discoloration in Polyurethane Foam

Liquid polymeric colorant ReacTint® Blue X3LV (available from Milliken Chemical) is widely used for the coloration of polyurethane foam, and is known to be very prone to UV discoloration. Thus, the blue foams were made in the presence of 1 php Blue X3LV with or without inventive UV absorber, in accordance with formulation and process as described in Section a). The foam buns were sliced in half, and small pieces of foam samples (diameters of 10 cm×5 cm×2 cm) were cut from the center of each foam bun. These foam samples were all tested under Xenon lamp chamber (AATCC Test No. 16-1999) for discoloration at different exposure time. Those foam samples exposed different amount of time under Xenon light were then compared reading in CMC for delta E with respected unexposed foam samples. The results are summarized in Table 3.

TABLE 3

Stabilization of RT Blur X3LV with Inventive UV Absorbers

| Sample Foam # | X3LV loading | UV Absorber | UVA Loading | LF (1 h) (delta E) | LF (2 h) (delta E) | LF (5 h) (delta E) | LF (10 h) (delta E) |
|---|---|---|---|---|---|---|---|
| A9 | 1 php | None | N/A | 11.2 | 11.4 | 11.7 | 11.3 |
| A10 | 1 php | Example 9 | 1 php | 4.8 | 5.5 | 10.5 | 11.7 |

Thus, without UV absorber, Blue X3LV was completely discolored after 1 hour of exposure under Xenon light. However, the discoloration of Blue X3LV foam made in the presence of the inventive UV absorber (1 php) from Example 9 showed significant improvement as evidenced in delta E measurement.

e) Reduction of Discoloration in White Polyurethane Foam

Several white foams made in accordance with formulation and process as described in Section a), in the presence of unique anti-discoloration additive packages consists of a UV absorber selected from Class A, a phenolic antioxidant from Class B, a secondary amine antioxidant from Class C and a lactone antioxidant from Class D. The inventive liquid polymeric UV absorbers are used in this unique additive package to replace the commercial UV absorbers which are solid and/or non-reactive. Upon the foams are made with the inventive additive packages, as well as commercially available additive packages, the foam buns are then sliced in half, and compared the performance against UV discoloration (Xenon lamp test according to AATCC Test No. 16-1999) and gas fading (AATCC Test No. 23-1999).

The inventive synergistic additive composition packages are listed in Table 4. Also included in Table 4 as comparatives, are control (with no additive) and commercially available additive packages B-75 (Ciba), CS-31 (Crompton) and LS-1 (Ortegol), which are current best commercial products in polyurethane industry for stabilization of white polyurethane foams.

TABLE 4

Additive Compositions and Loadings in Foam Formulation

| Additive package | UV Absorber (php) | Class B (php) | Class C (php) | Class D (php) |
|---|---|---|---|---|
| AA | Tinuvin 326 (1.5) | Irgnox 1135 (0.33) | Irgnox 5057 (0.50) | HP-136 (0.57) |
| BB | Example 9 (1.5) | Irgnox 1135 (0.33) | Irgnox 5057 (0.50) | HP-136 (0.57) |
| CC | Example 9 (2.0) | Irgnox 1135 (0.33) | Irgnox 5057 (0.50) | HP-136 (0.57) |
| DD | Example 9 (3.0) | Irgnox 1135 (0.33) | Irgnox 5057 (0.50) | HP-136 (0.57) |
| EE | Example 9 (3.8) | Irgnox 1135 (0.33) | Irgnox 5057 (0.50) | HP-136 (0.57) |
| FF | Example 11 (1.7) | Irgnox 1135 (0.33) | Irgnox 5057 (0.50) | HP-136 (0.57) |
| GG | Tinuvin B75 (commercially available from Ciba), loading @ 3.0 php | | | |
| HH | CS-31 (commercially available from Crompton), loading @ 3.0 php | | | |
| JJ | LS-1 (commercially available from Goldschmidt), loading @ 3.0 php | | | |
| Control | 0 | 0 | 0 | 0 |

Lightfastness and gas fade test results for the inventive and comparative sample foams are summarized in Table 5.

TABLE 5

Test Results for Inventive and Comparative Additive Packages

| Sample Foam # | Additive Package | Lightfastness delta E (13 hrs) | Gas Fade delta E (2 hrs) | Gas Fade delta E (4 hrs) |
|---|---|---|---|---|
| A11 | Control (N/A) | 34.6 | 34.2 | 56.2 |
| A12 | AA | 8.7 | 8.8 | 21.2 |
| A13 | BB | 17.8 | 9.2 | 27.4 |
| A14 | CC | 17.0 | 6.3 | 11.2 |
| A15 | DD | 11.9 | 3.8 | 10.4 |
| A16 | EE | 7.2 | 3.6 | 10.8 |
| A17 | FF | 11.3 | 13.6 | 31.1 |
| A18 | GG | 15.8 | 34.1 | 82.5 |
| A19 | HH | 18.2 | 51.4 | 53.1 |
| A20 | JJ | 13.5 | 37.3 | 53.6 |

Clearly, the inventive additive packages containing the inventive liquid polymeric UV absorbers exhibited the best overall performance against discoloration of UV exposure and gas fade, comparing to state-of-the-art commercial additive packages such as GG, HH and JJ. More over, when used at equal mole loading (based on different molecular weights of respected UV absorbers), the additive package containing the inventive liquid reactive polymeric UV absorber has significantly better performance than that containing solid non-reactive commercial UV absorber such as Tinuvin 326; especially when exposed to $NO_x$ gas discoloration tests.

f) Application of the Inventive UV Absorbers in PET Packaging

UV absorbers are being increasingly used in PET packaging to protect the content from UV degradation in the food container industry. Since UV absorbers could decompose during the injection molding process at process condition (usually 280° C.) causing resin yellowing, the appearance (yellowness index) the final PET articles (containing UV absorbers) becomes an indicator for the suitability of UV absorbers in this application. Another requirement for an acceptable UV absorber is the lightfastness of the UV absorber itself. The inventive liquid polymeric UV absorbers were thus tested for their performance against current best commercial products ClearShield® UV absorbers (available from Milliken Chemical).

In each instance noted below regarding polyester article production applications, the inventive polymeric UV absorber was introduced within an injection molding operation for a polyester thermoplastic, in this instance polyethylene terephthalate (ClearTuf® 8006 PET resin from M&G). The inventive UV absorber, in the amount noted in the related examples below, was blended via agitation onto hot, dried PET resin pellets. The blend of UV absorber and pellets was gravity fed into the feed throat of the machine. In the feed section, melting was accomplished through the utilization of rotating heated (heat transferred from the barrel of the machine) screw extruder. The rotation of the screw provided thorough mixing of the UV absorber and molten resin together producing a uniform plastic melt which was injected into a mold in order to form the thermoplastic article, in this instance a 2 inch by 3 inch plaque with a uniform thickness of 50 mils and a surface area of 12.5 $in^2$.

Ten 50 mil-thick plaques of UV absorber-containing PET, as made above, thermoplastic plaques of polyester terephthalate containing inventive UV absorber were produced as described above (injection molded) were collected. The same injection molding machine used to produce these first ten plaques was paused during production of ten further plaques and allowed to remain idle for 15 minutes at the standard polyester processing temperatures (~277° C.). At the end of the 15-minute pause, the machine was then restarted without purging the colored resin from the heated barrel of the machine. Ten consecutive plaques were then collected and numbered after resumption of the injection molding operation.

The absorbance at the UV absorber lambda max of the Control Samples collected from the standard operation was measured by Perkin-Elmer Lambda 35 Spectrophotometer and averaged together to represent a standard measurement for all plaques. Each of the ten consecutive Measured Sample plaques collected after the 15-minute hold-period was measured individually and sequentially on the spectrophotometer. The absorbance difference between the standard measurements for the Control Samples each of the ten Measured Sample plaques was recorded and defined as the change in absorbance (ΔAbs). The thermal stability of UV absorber was measured by the percentage of UV absorbance loss (Loss %), as calculated by the formula Loss %=[ΔAbs]/[standard]

The biggest Loss % of the ten Measured Samples plaques collected after the 15-minute hold period represents the largest absorbance difference, and is determined to be the UV absorber's thermal stability.

The thermal stability (Loss %) of the inventive UV absorbers from Example 9, above., as well as comparative commercial UV absorbers (ClearShield® UV absorbers) were measured, and the results are tabulated in Table 6 (the loadings for UV absorbers were adjusted to the same heights of the absorption peaks based on their Color Values).

TABLE 6

Inventive and Comparative UV Absorber Thermal Stability in PET

| UV Absorber | Loading (ppm) | % loss (50 mil) |
|---|---|---|
| Example 9 | 375 | Not Detectable |
| ClearShield ® UV390B | 200 | 2.7 |
| ClearShield ® UV400 | 275 | 8.9 |

A Loss % of less than 10 is considered to be acceptable, with a result less than 2 considered to be outstanding when analyzed by this protocol. Clearly, the inventive UV absorbers exhibited highly favorable thermal stability characteristics with no detectable loss, particularly in comparison with current best commercial products.

For each individual inventive or comparative UV absorber compositions at specified loadings (below), ten 50 mil-thick plaques were made according to process described as above in the previous section.

The absorbance (at each UV absorber's lambda max) of the ten plaques collected from the standard operation was measured in Perkin-Elmer Lambda 35 Spectrophotometer and averaged together to represent the Standard Measurement. Three sets of 2 plaques were then placed under xenon light for 20 and 40 hours exposure, respectively. Each set of the 2 plaques was collected after the elapsed times of exposure and were measured for change in absorbance (at each UV absorber's lambda max) individually and sequentially on a Perkin-Elmer spectrophotometer. The absorbance difference between the Standard Measurement and each of the 2 sets of plaques exposed was determined as ΔAbs. The lightfastness of the UV absorber incorporated was thus measured by the percentage of UV absorbance loss (Loss %), as calculated by the formula Loss %=[ΔAbs]/[Standard]

The greater the Loss % of the plaques, the larger the absorbance difference and is determined to be worse the UV absorber's lightfastness. The test results are summarized in Table 7.

TABLE 7

Lightfastness of the Inventive and Comparative UV Absorbers

| UV Absorber | Loading | Exposure Time | Loss % |
|---|---|---|---|
| Example 9 | 5000 ppm | 20 hours | 2.3 |
|  |  | 40 hours | 3.6 |
| ClearShield ® UV390B | 1450 ppm | 20 hours | 5.5 |
|  |  | 40 hours | 6.2 |
| ClearShield ® UV400 | 2000 ppm | 20 hours | 12.3 |
|  |  | 40 hours | 13.8 |
| Tinuvin ® 327 | 2500 ppm | 20 hours | 5.2 |
|  |  | 40 hours | 6.8 |

Under this protocol, a Loss % of at most 15% after 40 hours exposure is highly desired. This shows that the Inventive UV absorber provides significantly improved lightfastness characteristics over the comparative commercial products.

The degree of yellowing as a result of processing was determined for selected UV absorber examples. A specified amount of inventive and comparative UV absorbers were added to 2 kg of ClearTuf® 8006 polyester resin. After thorough mixing, the resin was compounded on a Single-Screw extruder and the emergent strands of material were pelletized. To simulate the industrial drying process commonly practiced by the converters, the pelletized sample was dried at 150° C. under vacuum for five hours and afterwards injection molded into 175 mil thickness plaques (2 in×3 in). The degree of yellowing of the plaques, expressed as Yellowness Index (ASTM Test Method E-313) was quantified with the aid of a MacBeth Coloreye 7000 spectrophotometer.

The yellowness of the inventive and comparative UV absorbers in 175 mil PET plaques were measured; and the results are tabulated in Table 8.

TABLE 8

Yellowness of the Inventive and Comparative UV Absorbers in Molded PET

| UV Absorber | Loading (ppm) | % Transmission @ 390 nm (15 mil) | Yellowness (175 mil) |
|---|---|---|---|
| PET Control | — | 99 | 1.9 |
| Example 9 | 5000 | 4.5 | 12.7 |
| ClearShield ® UV390B | 1450 | 4.1 | 15.3 |
| ClearShield ® UV400 | 2000 | 4.1 | 21.5 |

Less than 5% transmission of UV radiation at 390 nm in a 15 mil thick wall container is the best UV protection currently industry can achieve. The UV absorber loadings are adjusted based on the absorption strength to achieve this goal. ClearShield UV 390B is a long wavelength UV absorber. When used it alone in standard PET resin, it could not completely cover short wavelength UV radiation. At a loading of 1450 ppm UV 390B, a portion of UV radiation between 300-350 nm is still transmitted. In the above table, only the inventive UV absorber from Example 9 and ClearShield UV 400, at respected loadings, achieved less than 5% transmission at 390 nm.

Under this testing protocol, a Yellowness of at most 25 at the suggested loading levels is considered to be acceptable. Thus, the inventive UV absorber exhibited significantly better yellowness rating than the comparatives, showing the unexpectedly good results provided thereby.

g) Application of the Inventive UV Absorbers in Polypropylene

UV absorbers are commonly used in transparent polyolefin packaging such as films, containers, etc. to combat the harmful UV light. Two of the most widely used commercial UV absorbers are Tinuvin® 326 and 327. Since they are low molecular weight solids, their blooming and migration out of polypropylene composition during and/or after the injection molding process, is one of a few highly undesirable characteristics. The inventive liquid polymeric benzotriazole UV absorbers are thus tested for suitability in polypropylene application. The protocols for thermoplastic composition formation as well as their performance evaluations were similar to those as described above, and in U.S. Pat. No. 6,207,740. Table 9 summarized the Yellowness Index results.

TABLE 9

Loadings and Yellowness of the Inventive and Comparative UV Absorbers

| UV Absorber | Mw | Loading (ppm) | % Transmission @ 390 nm (25 mil) | Yellowness (50 mil) |
|---|---|---|---|---|
| Tinuvin 326 | 316 | 1200 | 10 | 6.3 |
| Example 9 | 803 | 2700 | 10 | 7.2 |

A yellowness of less than 10 is considered to be highly desirable for this application under this test protocol. Thus both inventive and comparative UV absorbers offered acceptable yellowness performance.

Additionally, although both inventive liquid polymeric UV absorber from Example 9 and commercial product Tinuvin 326 exhibited excellent thermal stability and lightfastness (after 20 and 40 hours exposure to Xenon light), the inventive UV absorber demonstrated a dramatically improved performance in extraction and plate-out tests. Being liquid in natural and with much improved migration, the inventive liquid polymeric UV absorber offers more desirable characteristics for polypropylene applications such as in packaging and in films and the like.

While specific features of the invention have been described, it will be understood, of course, that the invention is not limited to any particular configuration or practice since modification may well be made and other embodiments of the principals of the invention will no doubt occur to those skilled in the art to which the invention pertains. Therefore, it is contemplated by the appended claims to cover any such modifications that incorporate the features of the invention within the true meaning, spirit, and scope of such claims.

It is understood by one of ordinary skill in the art that the present discussion is a description of exemplary embodiments only, and is not intended as limiting the broader aspects of the present invention, which broader aspects are embodied in the exemplary constructions. The invention is shown by example in the appended claims.

What is claimed is:

1. A compound represented by the formula:

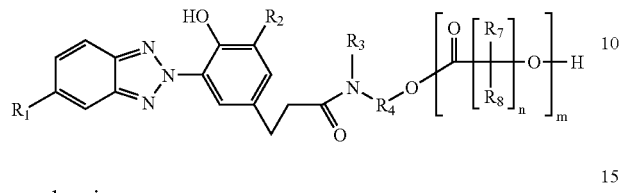

wherein:
$R_1$ is selected from the group consisting of: H, F, Cl, Br, I, alkyl, alkoxy, carbonyl-containing groups represented as —C(O)-A, and $SO_2$-containing radicals represented as $SO_2$-A; wherein A is selected from OH, alkyl, alkoxy, and organic amine groups;
$R_2$ is selected from the group consisting of: H, $C_1$-$C_{10}$ alkyls, and $C_7$-$C_{20}$ phenylalkyls;
$R_3$ is selected from the group consisting of: H, carbon containing chain radicals, and carbon/oxygen containing chain radicals;
$R_4$ is selected from the group consisting of: divalent $C_2$-$C_{20}$ alkyl radicals, divalent $C_4$-$C_{20}$ alky radicals interrupted by oxygen, sulfur or nitrogen, and divalent oligomeric radicals;
$R_7$ and $R_8$ each are independently selected from the group consisting of: H and $C_1$-$C_{10}$ alkyl groups;
n is an integer between 1 and 10; and
m is a positive integer or fraction thereof between 1 and 20.

2. The compound of claim 1 wherein m is at least 2.
3. The compound of claim 1 wherein n is at least 2.
4. The compound of claim 2 wherein $R_3$ is H.
5. The compound of claim 3 wherein $R_3$ is H.
6. The compound of claim 4 wherein $R_1$ is Cl or H.
7. The compound of claim 5 wherein $R_1$ is Cl or H.
8. The compound of claim 6 wherein $R_2$ is a tert-butyl group.
9. The compound of claim 7 wherein $R_2$ is a tert-butyl group.
10. The compound of claim 8 wherein n is 5.
11. The compound of claim 10 wherein m is at least 3.
12. The compound of claim 10 wherein $R_4$ is a divalent radical selected from the group consisting of: —$CH_2CH_2$—, —$CH_2CH_2OCH_2CH_2$—, —($CH_2CH_2O)_2$—$CH_2CH_2$—, and —($CH_2)_3O(CH_2CH_2O)(CH_2CH_2)$—.
13. The compound of claim 11 wherein $R_4$ is a divalent radical selected from a group consisting of: —$CH_2CH_2$—, —$CH_2CH_2OCH_2CH_2$—, —($CH_2CH_2O)_2$—$CH_2CH_2$—, and —($CH_2)_3O(CH_2CH_2O)(CH_2CH_2)$—.
14. An article comprising:
(a) at least one polymeric formulation having a thermoplastic or thermoset component, or mixtures thereof; and
(b) at least one UV absorbing compound, wherein the UV absorbing compound is either (i) present within said polymeric formulation or (ii) adhered to the surface of said polymeric formulation,
wherein said UV absorbing compound conforms to the structure below:

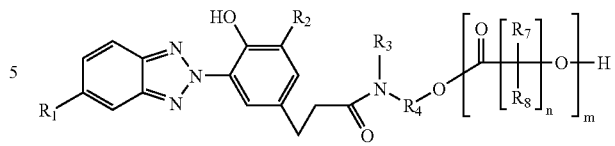

wherein:
$R_1$ is selected from the group consisting of: H, F, Cl, Br, I, alkyls, alkoxy, carbonyl-containing radicals represented as —C(O)-A, and $SO_2$-containing radicals represented as $SO_2$-A, wherein A is OH, alkyl, alkoxy, or an organic amine group;
$R_2$ is selected from the group consisting of: H, $C_1$-$C_{10}$ alkyls, and $C_7$-$C_{20}$ phenylalkyls;
$R_3$ is selected from the group consisting of: H, carbon-containing chain radicals, oxygen-containing chain radicals, and nitrogen-containing chain radicals;
$R_4$ is selected from the group consisting of: divalent $C_2$-$C_{20}$ alkyl radicals, divalent $C_4$-$C_{20}$ alky radicals interrupted by oxygen, sulfur or nitrogen, and divalent oligomeric radicals;
$R_7$ and $R_8$ each are independently selected from H or $C_1$-$C_{10}$ alkyl groups;
n is an integer between 1 and 10; and
m is any positive integer or fraction between 1 and 20.

15. The article of claim 14 wherein m is at least 3.
16. The article of claim 14 wherein n is at least 3.
17. The article of claim 14 wherein $R_3$ is H.
18. The article of claim 14 wherein $R_3$ comprises a carbon containing chain radical.
19. The article of claim 14 wherein $R_3$ comprises an oxygen containing chain radical.
20. The article of claim 14 wherein:
$R_1$ is Cl or H;
$R_2$ is a tert-butyl group; and
$R_7$ and $R_8$ each is H; and
n is 5.
21. The article of claim 14 wherein
$R_1$ is Cl or H;
$R_2$ is tert-butyl group;
$R_7$ and $R_8$ each is H;
n is 5; and
m is 3.
22. The article of claim 14 wherein $R_4$ comprises a divalent radical selected from a group consisting of: —$CH_2CH_2$—, —$CH_2CH_2OCH_2CH_2$—, —($CH_2CH_2O)_2CH_2CH_2$—, and —($CH_2)_3O(CH_2CH_2O)(CH_2CH_2)$—.
23. The article of claim 14 wherein said polymeric formulation comprises at least one thermoplastic component.
24. The article of claim 23 wherein said thermoplastic component comprises at least one organic material selected from the group consisting of:
polyolefins, polyesters, polycarbonates, thermoplastic polyurethanes, and polyamides.
25. The article of claim 14 wherein said polymeric formulation comprises polypropylene.
26. The article of claim 14 wherein said polyester chain comprises polyethylene terephthalate (PET).
27. The article of claim 14 wherein said polymeric formulation comprises at least one thermoset component.

28. The article of claim 27 wherein said thermoset component comprises at least one organic material selected from the group consisting of:
polyurethanes and acrylic resins; wherein said organic material is capable of being cross-linked by heat.

29. The article of claim 28 wherein said polyurethane comprises a polyurethane foam.

30. The article of claim 14, wherein said UV absorbing compound is present in the amount from about 0.1 to 15% by weight of said polymeric formulation.

31. The article of claim 30, wherein said UV light absorbing compound is present in the amount of 0.3 to 8% by weight of said polymeric formulation.

32. The article of claim 30, wherein said UV light absorbing compound is present in the amount of 0.5 to 5% by weight of said polymeric formulation.

* * * * *